(12) United States Patent
Phinney et al.

(10) Patent No.: US 9,314,412 B2
(45) Date of Patent: Apr. 19, 2016

(54) DEODORANT FORMULATION

(71) Applicants: Robin Phinney, Okotoka (CA); Jonathon Phinney, Martensville (CA)

(72) Inventors: Robin Phinney, Okotoka (CA); Jonathon Phinney, Martensville (CA)

(*) Notice: Subject to any disclaimer, the term of this patent is extended or adjusted under 35 U.S.C. 154(b) by 277 days.

(21) Appl. No.: 13/803,387

(22) Filed: Mar. 14, 2013

(65) Prior Publication Data

US 2014/0271517 A1    Sep. 18, 2014

(51) Int. Cl.
| | |
|---|---|
| *A61K 8/27* | (2006.01) |
| *A61K 8/23* | (2006.01) |
| *A61Q 15/00* | (2006.01) |
| *A61K 8/19* | (2006.01) |
| *A61K 8/34* | (2006.01) |
| *A61K 8/36* | (2006.01) |
| *A61K 8/20* | (2006.01) |

(52) U.S. Cl.
CPC ... *A61K 8/27* (2013.01); *A61K 8/19* (2013.01); *A61K 8/20* (2013.01); *A61K 8/23* (2013.01); *A61K 8/345* (2013.01); *A61K 8/361* (2013.01); *A61Q 15/00* (2013.01)

(58) Field of Classification Search
CPC ............. A61K 8/27; A61K 8/23; A61K 8/19; A61Q 15/00
See application file for complete search history.

(56) References Cited

U.S. PATENT DOCUMENTS

| | | | |
|---|---|---|---|
| 3,943,242 A * | 3/1976 | Fogel et al. ...................... 424/65 |
| 2007/0202062 A1* | 8/2007 | Workman et al. ................ 424/66 |
| 2011/0229427 A1* | 9/2011 | Klug et al. ....................... 424/66 |

* cited by examiner

*Primary Examiner* — Ali Soroush
*Assistant Examiner* — Genevieve S Alley
(74) *Attorney, Agent, or Firm* — Craig J. Lervick; Larkin Hoffman Daly & Lindgren, Ltd.

(57) ABSTRACT

Deodorant formulations are provided. The formulations all commonly include magnesium oxide, zinc oxide and as a disinfecting agent, potassium chloride and/or potassium sulphate. The combination provides long lasting odor protection since the disinfectant destroys odor causing microorganisms. The formulations all contain natural ingredients and the absence of petroleum based or related synthetic compounds contributes to the efficacy of the formulations.

7 Claims, No Drawings

DEODORANT FORMULATION

TECHNICAL FIELD

The present invention relates to a deodorant formulation and more particularly, the present invention relates to such a formulation and preparation thereof with natural ingredients in the absence of heavy metal complexes and/or petroleum based or related compounds.

BACKGROUND OF THE INVENTION

In a previous adaptation, Robin Phinney, in U.S. Pat. No. 5,512,274, issued Apr. 30, 1996, taught a metal hydroxide deodorant formulation. In this document, milk of magnesia or magnesium hydroxide was found to be an effective deodorant. It was also found that a mixture of the hydroxides of zinc and magnesium could provide long lasting protection against odour due to perspiration. The previous teachings provided that these materials are active ingredients, and are dispersible in aerosols, moisturizing creams, sticks, sprays and roll-on type applicators.

The active hydroxide neutralizes 3-methyl-2-hexanoic acid and similar materials are largely responsible for body odour associated with perspiration. These weak organic acids are produced by a bacterial action and require a moderately strong hydroxide type base to neutralize them and eliminate odour associated with, but not confined to perspiration.

A vast array of compounds have been purported to combat perspiration and perspiration odour. In U.S. Pat. No. 3,996,346 issued Dec. 7, 1976, to Staffier et al., a range of acidic to neutral to basic salts are proposed as active ingredients to reduce body odour and/or stem perspiration. Many of the salts cited in the patent can be injurious to the skin. Acid salts such as aluminum chloride, for example, hydrolyze to form hydrochloric acid, which can be injurious to both skin and clothing. Potassium alum has become widely available, and while effective as a deodorant, it hydrolyzes to form even more injurious sulphuric acid as well as aluminum in a soluble ionic form, which can lead to higher rates of absorption into the body than is the case with aluminum metal or alumina.

These salts have hydrolysis points or protolysis reactions because they hydrolyze at different points on the pH scale (Chemistry of the Elements, Greenwood and Earnshaw, 1984) and precipitate out of solution, primarily as hydroxides, at various pHs. For example, ferric hydroxide precipitates or hydrolyzes out of solution a pH of about 2.6 to 4.0 while aluminum hydroxide precipitates or hydrolyzes out of solution in the range of 3.6 to 4.2.

Other salts, such as zinc, precipitate as hydroxides in the range of 6.5 to 8.0, but salts of these materials can behave in an erratic manner with many individuals in that they work effectively for very irregular periods of time. In addition, zinc sulphate still releases sulphuric acid upon hydrolysis. The sporadic efficacy may be due to lack of hydrolysis, conversion to relatively inactive carbonate or oxide, or some combination of these factors.

Basic materials have been proposed, such as in U.S. Pat. Nos. 74,871; 1,558,406; 2,114,559; and 2,187,163, however, there are problems with most of these materials.

The carbonates of U.S. Pat. No. 74,871, issued Feb. 25, 1868, to Wilson, are very soluble and quickly leach from the skin during perspiration.

The active agent of U.S. Pat. No. 1,558,406, a hexametaphosphate, is soluble and liable to be washed away during perspiration. Being a phosphate, this agent could well serve as a major nutrient source of the bacteria believed to be responsible for body odour and this agent could thereby promote body odour rather than diminish it.

U.S. Pat. No. 1,558,405, issued May 3, 1983, to Marschner, contains mention of some of the same basic materials mentioned in U.S. Pat. No. 74,781 and includes "sodium bicarbonate, potassium bicarbonate, sodium or potassium carbonate, calcium hydroxide and the like . . . ". The term "and the like" is vague, nebulous, undefined and unspecified given the previous explicit identification of agents. Materials mentioned, such as potassium carbonate and lime, are very basic and could injure skin and clothing. This patent claims that basic agents need to be combined with "an absorptive insoluble filler material of emollient character, such as the stearate of zinc, aluminum or magnesium, or a mixture of talc and small portions of zinc oxide". The basic materials were said to lead to a drying action, which is offset by the healing action of the emollient. The patent does not prescribe deodorant formulations consistent with current understanding of mitigation of body odour due to perspiration.

While bases in high concentration may have "drying action", they primarily neutralize acids as is evident to those skilled in the art. The only "anti-acid" body listed in the claims, which if compatible with the body, is sodium bicarbonate. It is not capable of neutralizing the agents responsible for body odour.

The patent does not teach that if the formulations had any significant efficacy, it did not arise from the action of the basic agent, sodium bicarbonate, cited in the claim but from some other material or combination of materials. Metal stearates, the so-called "absorptive insoluble filler material of an emollient character" of the formulation, might, under some circumstances, be responsible for some, if any, activity associated with the formulation cited in this patent. Another possibility is zinc oxide, but it along with many other "basic" metal oxides like alumina are very unreactive against perspiration odour due to insolubility and low hydrolysis rate to a hydroxide form that could show some activity.

The filler materials are first and foremost sparingly soluble neutral metallic salts of a weak organic acid which would only be weakly hydrolyzed to a potentially active agent with the aluminum salt having the best potential for any efficacy due to its low hydrolysis pH.

The zinc salts would show some erratic behaviour as noted before but would be strongly inhibited by being coupled to a weakly dissociated organic acid. The magnesium salt would be no more effective than Epsom salts since it has no capacity of generate basic deodorizing agent through dissolution in water.

The zinc stearate cited as the emollient could have some antiperspirant activity but is likely subject to the erratic activity noted earlier for zinc salts. The stearate portion could supply organic material to foster undesirable bacterial growth and therefore be undesirable.

U.S. Pat. No. 2,187,163, issued Jan. 16, 1940, to Langer, identifies the use of "base" carrier materials such as kaolin or calamine with the latter being preferred when combined with active deodorant materials such as aluminum and zinc chloride. Calamine, zinc oxide and sulphates of aluminum and zinc are claimed as active agents. It is said that these formulations supplanted with other agents such as tannic acid and/or salicylic acid "have the property of preventing or reducing perspiration and of acting as deodorants in this manner".

Oxides and carbonates of "acceptable" antiperspirant agents, such as alumina and calamine, are generally ineffective in reducing body odour because they are inactive with respect to the weak organic acid responsible for perspiration odour for reasons of equilibrium, kinetics and solubility. Sulphates of zinc, unlike those of aluminum, have been observed to be erratic performers likely because they do not hydrolyze effectively. The author claims that the sulphates of aluminum and zinc have the property of reducing or preventing perspiration and act as deodorants in this manner.

There is no evidence in the text to support this assertion and it is evident to those skilled in the art that neither compound would act to any significant extent as a desiccant. These agents most likely act in a different manner and understanding of the mechanism of this action could result in a significantly different approach in formulating materials with greater efficacy.

Body odour is known to those skilled in the art to be due primarily to the products of bacterial action and not moisture as such.

U.S. Pat. No. 3,996,346, issued Dec. 7, 1976, to Staffier et al., cites zinc oxide and calcium hydroxide along with phenol as an effective deodorant. As is evident by the citation of U.S. Pat. No. 1,558,405, the use of lime as deodorant agent has been noted some time ago. Given the low activity of zinc oxide as a deodorant agent, it is likely that any observed deodorant activity is due to the lime. Lime is quite basic with reported pHs of 12.5 and higher. While lime has the capability to function as an effective agent against odour, it is less desirable than other agents due to its alkalinity. The zinc oxide combined with stearic acid as a cream base most likely is an attempt to minimize the undesirable effects due to high alkalinity and the general undesirable nature of phenyls in skin care products.

Since the initial formulation was disclosed in U.S. Pat. No. 5,512,794, there have been several hundred additional patents issued with a like number of applications filed. As an example, United States Patent Application Publication US2008/0131387, filed Dec. 6, 2007 and published Jun. 5, 2008, provides for a liquid stick antiperspirant. The disclosure indicates that the formulation contains materials for preserving the stability of the formulation. To this end, a number of petroleum based compounds are used.

In U.S. Pat. No. 7,703,767, issued Dec. 4, 2007, to Withiam et al., a personal care formulation is disclosed. The formulation coats metal silicates for improved odour neutralization. Although useful, the formulation incorporates several synthetic compounds which inherently limits the efficacy.

In summary, there is a wide range of active ingredients cited in the open and patent literature for prevention of body odour and perspiration but most have some undesirable characteristics. Many formulations use aluminum chloride or other aluminum compounds based on sulphates for example that form irritating acids. As well, human exposure to aluminum is raising health concerns. Other formulations recommend materials, such as potassium carbonate, that can be harmful to the skin, or salts of zinc that have minimal efficacy due to poor hydrolysis to active hydroxide.

There is, therefore, a need to provide alternative deodorant formulations that balance the need for performance, efficacy, simplicity, and compatibility of the formulation with good health care in conjunction with a technically sound understanding of the reason for body odour and therefore the correct abatement measures to take.

SUMMARY OF THE INVENTION

This invention aids in fulfilling these needs in the art.

One object of one embodiment of the present invention is to provide a deodorant formulation, comprising a polyol, glycerine; a disinfectant agent comprising at least one of potassium chloride and potassium sulphate for destroying microorganisms associated with odour; zinc oxide; magnesium oxide; sodium stearate; water; and a cosmetically acceptable filler.

The content of the zinc oxide and magnesium oxide can vary in the case of zinc oxide between 0.5% to 10% by weight of the formulation. In a specific example, the range will be between 0.5% and 1.5% by weight of the formulation; in respect of the magnesium oxide, the amount can vary from between 1% and 10% by weight of the formulation with a specific example being between 1.5 and 2.5% by weight.

A further object of one embodiment is to provide a deodorant formulation comprising: propylene glycol in an amount of between 52% and 57% by weight of said formulation; glycerine in an amount of between 6% and 10% by weight of said formulation; a disinfectant agent comprising at least one potassium chloride and potassium sulphate in an amount of between 0.5% and 1% by weight of said formulation for destroying microorganisms associated with odour; zinc oxide in an amount between 0.5% and 1.5% by weight of said formulation; magnesium oxide in an amount between 1.0% and 2.5% by weight of said formulation; sodium stearate in an amount between 4% and 8% by weight of said formulation; water in an amount between 18% and 22% by weight; and a balance of a cosmetically acceptable filler.

A further object of another embodiment is to provide a deodorant formulation, comprising a solid stick based deodorant formulation, comprising a propylene glycol in an amount of between 52% and 57% by weight of said formulation; glycerine in an amount of between 6% and 10% by weight of said formulation; a disinfectant agent comprising at least one potassium chloride and potassium sulphate in an amount of between 0.5% and 1% by weight of said formulation for destroying microorganisms associated with odour; zinc oxide in an amount between 0.5% and 1.5% by weight of said formulation; magnesium oxide in an amount between 1.0% and 2.5% by weight of said formulation; sodium stearate in an amount between 4% and 8% by weight of said formulation; water in an amount between 18% and 22% by weight; a cosmetically acceptable thickener in an amount sufficient to provide a consistency for said formulation; and the balance comprising water.

In both of these embodiments, the disinfecting and deodorizing formulations can be used as precursory mixture for other formulations and uses.

As a further object of one embodiment of the invention, there is provided is a method of formulating a deodorant formulation, comprising providing magnesium oxide, zinc oxide and potassium sulfate or potassium chloride; mixing said magnesium oxide and said zinc oxide components of step a) with water to convert said components to their respective hydroxides; mixing a polyol into the mixture; heating said mixture to 80° C.; emulsifying said mixture with the addition of sodium stearate; maintaining the emulsified mixture at a temperature between 60° C. and 80° C. to remove any trapped gas; and cooling said mixture to slightly above the solidification point.

Yet another object of one embodiment is to provide a method of formulating a deodorant composition, comprising: providing MgO, ZnO and potassium sulfate or potassium chloride; mixing said magnesium oxide and said zinc oxide components of step a) with water to convert said components to their respective hydroxides; mixing a polyol into the mixture; heating said mixture to 80° C.; emulsifying said mixture with the addition of sodium stearate; maintaining the emulsified mixture at a temperature between 60° C. and 80° C. to remove any trapped gas; and cooling said mixture to slightly above the solidification point.

A still further object of one embodiment is to provide a deodorant formulation, comprising by weight of the formulation: 55% propylene glycol; 20% water; 12% glycerine; 8% Sodium Stearate; 2.5% MgO; 1.5% ZnO; and 1% KCl.

DETAILED DESCRIPTION OF THE PREFERRED EMBODIMENTS

It has been discussed in U.S. Pat. No. 5,512,274, that there are problems associated with the active agents used in many deodorant formulations as noted in the prior art. In searching for a suitable formulation, the objective was to find an agent or agents that acted as deodorants rather than antiperspirants. However, it will be evident to those skilled in the art that an agent effective as a deodorant could well be part of the basis for an antiperspirant formulation using materials obvious to those skilled in the art for the purpose of combating wetness.

As reported, certain organic acids, such as 3-methyl-2-hexanoic and others (George Preti of the Monell Chemical Senses Center in Philadelphia), are primarily responsible for disagreeable odours generally associated with perspiration and produced by microorganisms.

A previously presented solution was to neutralize the acid produced and thereby eliminate the odour of the acid by forming a salt of the hexanoic acid with a suitable base. Strong bases cited in the prior art, such as potassium carbonate, are not good because they are so basic that they cause skin damage and they are also so soluble that they rapidly wash away under heavy perspiration providing a very low duration of protection.

Conventional basic agents need to yield a pH of 9 to 10 as a minimum to be effective but not extend much above this level to avoid skin irritation. The base must behave in such a manner that it does not wash away like soluble carbonates or more simply, the base should be sparingly soluble and with the requisite pH requirements, function on a stand alone basis, and not be harmful to the skin.

At the same time, a metal hydroxide base is preferred due to its high activity compared to metal carbonates, such as limestone or other such benign carbonates, when trying to neutralize a weak organic acid. As well, a metal hydroxide is preferred over metal oxides since many show very low solubilities and negligible reactivities like alumina. Lime has been previously identified as a deodorant ingredient, but its high pH rules out direct application.

A suitable and simple agent previously presented in U.S. Pat. No. 5,512,274, before is magnesium hydroxide, (milk of magnesia). It has low solubility and therefore does not "wash away" under heavy perspiration. The pH is in the range of 10.0 and magnesium hydroxide provides 16-20 hour protection and more for a broad cross section of people.

The magnesium hydroxide incorporated in a formulation of the invention for controlling perspiration odour such that the formulation has a pH of about 9 to about 10.5. Preferably, the pH of the formulation is about 10. The formulations discussed herein include zinc hydroxide This combination provides for a pH of about 7.5 to about 10.5, preferably about 9 to about 10. The zinc hydroxide typically lowers the pH of the magnesium hydroxide-perspiration odour-controlling formulation of the invention.

It has now surprisingly been found that incorporation of a disinfectant with the platform of magnesium oxide and zinc oxide base has particular efficacy in destroying the microorganisms causing the odour. It is believed that the previously recognized synergy between the zinc and magnesium compounds has been further augmented with the disinfection capacity of a potassium and/or sulfate potassium chloride.

As an appealing benefit, the formulations do not contain aluminum compounds which, as discussed supra are contributory to acid synthesis coupled with potential health concerns. Further, the formulations do not contain any synthetic petroleum based products inherent in the vast majority of the existing formulations presently available. The formulations presented herein are natural minerals with organic thickeners all of which are water soluble and environmentally friendly.

Given the simplicity of the active ingredients in the formulation, the same lends itself to a variety of deodorant types. As an example, the formulation can be prepared as a stick, spray, gel, cream as well as precursor formulations of the active ingredients only to allow for subsequent final formulation by an end user as another deodorant product.

In keeping with the all natural ingredients, natural organic thickeners can be employed such as polysaccharides, a suitable example of which is Amigel, a trademark of the Alban Muller company. Other suitable examples include guar guar, carrageenan, xanthan, gum tragacanth, gum Arabic, gum karaya, locust bean gum inter alia. These are exemplary and not meant to be limiting. A broad range of possibilities is readily within the purview of one skilled.

Other agents may be incorporated into the formulation such as fragrance, spreadability enhancing agents, glide agents, moisturisers, cooling agents, etc. As an example, propanediol, a trademark of DuPont Tate & Lyle Bio Products, is a corn derived glycol which is known to provide a silky feeling with high stability and spreadability. These attributes are very beneficial for underarm deodorant formulations.

Turning to the specific formulations, in a first embodiment, the deodorant formulation includes magnesium oxide in an amount of between 1% and 2.5% by weight and zinc oxide in an amount of between 0.5% and 1.5% by weight. In order to further augment the efficacy of the formulation, a disinfectant agent is included. As an example, potassium sulfate in an amount of between 0.5% and 1% by weight. Propylene glycol in an amount between 45% and 57% by weight is included. Other polyols may be substituted such as glycenol, etc. Sodium stearate is also present in am amount between 4% and 8% by weight. Glycerin is also present in an amount from between 6% and 10% by weight. The balance of the formulation is obviously water. The sulphate compound has been found particularly effective in destroying the microorganisms responsible for the odour in perspiration. The provision for the suspension is very convenient, since the active ingredients are all present and this suspension can used as a precursor in the formulation of other deodorizing products.

It is envisioned that the formulation could be easily combined with soaps, detergents, fabrics etc. to form a panoply of deodorizing products.

In respect of the specific formulations, the same may take any number of actual forms; a cosmetically acceptable thickener in an amount sufficient to provide a gel consistency for the formulation is provided and may be chosen from those noted above. As an option, the formulation may also contain 1,3 propanediol for purposes of glide for comfort in application.

For the formulations of the invention ethyl alcohol may be included to act as a dispersant for the magnesium oxide and zinc oxide. In addition, the ethyl alcohol aids drying of the formulation on the surface to which the formulation is applied, thus avoiding extended wetness.

It will be understood that other materials that perform the functions associated with the ethyl alcohol can be used in combination with ethyl alcohol or substituted for the ethyl alcohol.

Although it may seem evident after an overview of the chemistry of acids, bases, salts, hydrolysis theory and the theory of odour due to perspiration, the combined use of magnesium oxide, zinc oxide together with a bactericidal agent for microorganism control has not been previously identified.

It is known from the earlier Phinney U.S. patent that metal hydroxides are active agents against body odour, together with zinc hydroxide, which is active even though it is more neutral than milk of magnesia. As well, zinc has a well known salutary effect on the skin. Several deodorant formulations use zinc oxide; however, as noted before, of the group of metal oxides that could be considered safe for human use, most hydrate to the active hydroxide form very slowly. For example, as in the Bayer aluminum process, strong caustic soda is required to transform alumina to the hydroxide form in high yield.

Sulphates and chlorides of zinc hydrolyze to zinc hydroxide in an erratic manner because the protolysis reaction is much less extensive than with aluminum chloride or potassium alum, for example.

Greenwood and Earnshaw refer to metal salt hydration as hydrolysis or protolysis reactions having some similarity to acidity scales. The literature, such as Chemical Reviews 1957 and Progress in Physical Organic Chemistry, document a variety of acidity and basicity scales based not only on the pioneering work of Louis P. Hammett but concepts such as carbon acidity and basicity.

Ralph G. Pearson proposed in 1966 (Journal of the American Chemical Society) a very broad concept of acids and bases called HSAB that went beyond the Bronstead and Lewis theory of acids and bases to include a wider range of phenomena that cover the concept of cation acidity, which can be used, in conjunction with solubility phenomena, to rationalise protolysis reactions as observed with salts such as aluminum chloride.

With an absorber such as body oils, HCl from aluminum chloride hydrolysis is absorbed. The aluminum cation is so "acidic" that it reacts with water as a "base" and forms aluminum hydroxide which can then neutralize hexanoic acid. At the other end of the scale, a salt like magnesium sulphate has a magnesium cation that cannot "hydrolyze" or has insufficient cation acidity to form magnesium hydroxide, and consequently cannot act as an effective deodorant. The formal hydroxide form of magnesium must be used for deodorant purposes.

Salts of the zinc do not have enough cation acidity to form zinc hydroxide to any effective degree except to the extent that most soaps impart some alkalinity causing the formation of zinc hydroxide. Hence the sporadic action of zinc salts and the need to use zinc oxide as a deodorant rather than zinc salts.

The above formulations of magnesium, zinc and sulfates can require moisturizing agents to ensure that there is available hydroxide in solution on the skin's surface. Neutral salts are preferred with lower solubilities being favored. Examples of suitable moisturizing agents are Epsom salts, Glaserite, and kainite.

The formulation of the invention can also contain a non-toxic, non-corrosive, double salt having water of hydration and a pH of about 5 to about 8 when dissolved in water. The double salt is employed in an amount sufficient to increase retention of the magnesium hydroxide, and zinc hydroxide, on the surface to which the formulation is applied in the presence of human perspiration. The double salt thus aids in minimizing the likelihood that the formulation of the invention will "wash away" in the presence of heavy perspiration.

The formulation of the invention can be applied to a surface in contact with human perspiration. Thus, for example, the formulation can be applied to the skin of a human, such as the underarm or foot areas. As another example, the formulation can be applied to a garment in contact with perspiration, such as a sock or shoe.

The admixture of zinc and magnesium oxides together with the sulfates has yielded deodorant protection for significant extended periods of time. In effect, the formulations offer a "double" degree of protection. One from the zinc and magnesium compounds previously discovered by Applicant and the second being the disinfectant action of the potassium chloride or potassium sulphate. Accordingly, even in the worst cases of perspiration, odour is checked, since the formulation incorporates the bactericidal agent.

Although embodiments of the invention have been described above, it is not limited thereto and it will be apparent to those skilled in the art that numerous modifications form part of the present invention insofar as they do not depart from the spirit, nature and scope of the claimed and described invention.

In respect of greater detail regarding the formulation, magnesium oxide and zinc oxide must have high reactivity and are added to water along with potassium sulfate and mixed until the magnesium oxide and zinc oxide are converted to their hydroxides. This generally occurs within an hour. The polyols are added and the mixture heated and stirred until the temperature reaches 80° C. At this point, sodium stearate is added slowly and the mixture is shear mixed to completely emulsify the mixture. The shear mixing is conducted for between 5 and 10 minutes.

The mixture is mixed normally and held at a temperature between 60° C. and 80° C. for approximately an hour to remove air bubbles. Color or fragrance may be added at this time. The mixture is then cooled to between 50° C. to 60° C., slightly above the solidification point and stirred vigorously and quickly poured into deodorant containers (not shown). The containers must be cooled quickly to between 20° C. and 40° C.

The magnesium oxide and zinc oxide must be completely converted to their hydroxides or skin irritation will occur.

The magnesium oxide and zinc oxide ratio has been found effective at 3:1 molar.

We claim:

1. A deodorant formulation in a solid stick form, comprising:
    a polyol;
    glycerine;
    at least one of potassium chloride and potassium sulphate;
    zinc hydroxide;
    magnesium hydroxide;
    sodium stearate;
    water; and
    a cosmetically acceptable filler;
    wherein said magnesium hydroxide and said zinc hydroxide are present in a molar ratio up to about 3:1.

2. The formulation as set forth in claim 1, wherein said polyol is propylene glycol.

3. A deodorant formulation in solid stick form, comprising:
    propylene glycol in an amount of from 52% to 57% by weight of said formulation;
    glycerine in an amount of from 6% to 10% by weight of said formulation;
    at least one of potassium chloride and potassium sulphate in an amount from 0.5% to 1% by weight of said formulation;

zinc hydroxide in an amount from 0.5% to 1.5% by weight of said formulation;
magnesium hydroxide in an amount from 1.0% to 2.5% by weight of said formulation;
sodium stearate in an amount from 4% to 8% by weight of said formulation;
water in an amount from 15% to 20% by weight; and
a balance of a cosmetically acceptable filler,
wherein said magnesium hydroxide and said zinc hydroxide are present in a molar ratio UP to about 3:1.

4. The formulation as set forth in claim 3, wherein said formulation further includes a member selected from the group consisting of a humectant, a glide agent, emollient, PABA, panthenol, lanolin, jojoba, ceramides, candela wax, beeswax, aloe vera, allantoin, anti-oxidants, butylene glycol, carbomers, caprylic/capric triglyceride, cetyl alcohol, cyclomethicone dimethicone, disodium emulsifying wax ethylparaben, glycerin, glyceryl stearate, hydrolyzed oat protein, methylparaben omental polysorbate 80, propylparaben, stearic acid, triethanolamine, Vitamin A, Vitamin C, Vitamin E or tocopherol acetate, and shea butter.

5. The formulation as set forth in claim 4, wherein said formulation further comprises a cosmetically acceptable thickener selected from the group consisting of guar guar, carrageenan, xanthan, gum tragacanth, gum Arabic, gum karaya, and locust bean gum.

6. The formulation as set forth in claim 3, further including a cosmetically acceptable fragrance.

7. A deodorant formulation in a solid stick form, comprising by weight of said formulation: 55% propylene glycol; 20% water; 12% glycerine; 8% Sodium Stearate; 2.5% MgOH; 1.5% ZnOH; and 1% KCl.

\* \* \* \* \*